United States Patent
Natan et al.

(10) Patent No.: US 7,892,726 B2
(45) Date of Patent: Feb. 22, 2011

(54) METHOD FOR STERILIZING LYOPHILIZED EUKARYOTIC ANUCLEAR CELLS WITH GAMMA IRRADIATION

(75) Inventors: Yehudit Natan, Holon (IL); Tamir Kanias, Givat Shmuel (IL)

(73) Assignee: Core Dynamics Limited, Hamilton (BM)

( * ) Notice: Subject to any disclaimer, the term of this patent is extended or adjusted under 35 U.S.C. 154(b) by 744 days.

(21) Appl. No.: 11/628,648

(22) PCT Filed: Jun. 7, 2005

(86) PCT No.: PCT/IL2005/000600
§ 371 (c)(1),
(2), (4) Date: Feb. 7, 2007

(87) PCT Pub. No.: WO2005/120591
PCT Pub. Date: Dec. 22, 2005

(65) Prior Publication Data
US 2008/0038818 A1  Feb. 14, 2008

Related U.S. Application Data

(60) Provisional application No. 60/577,210, filed on Jun. 7, 2004.

(51) Int. Cl.
A01N 1/02 (2006.01)
A01K 63/00 (2006.01)
C12N 7/04 (2006.01)
C12N 13/00 (2006.01)

(52) U.S. Cl. .............. 435/2; 435/173.1; 435/236; 424/93.72; 424/93.73

(58) Field of Classification Search .......... None
See application file for complete search history.

(56) References Cited

U.S. PATENT DOCUMENTS

| | | | |
|---|---|---|---|
| 3,074,247 A | 1/1963 | Polk | |
| 3,347,745 A | 10/1967 | Rinfret et al. | |
| 4,018,911 A | 4/1977 | Lionetti et al. | |
| 4,117,881 A | 10/1978 | Williams et al. | |
| 4,480,682 A | 11/1984 | Kaneta et al. | |
| 4,620,908 A * | 11/1986 | Van Duzer | 204/157.68 |
| 4,857,319 A | 8/1989 | Crowe et al. | |
| 4,874,690 A | 10/1989 | Goodrich, Jr. et al. | |
| 5,059,518 A | 10/1991 | Kortright et al. | |
| 5,071,598 A | 12/1991 | Baldeschwieler et al. | |
| 5,131,850 A | 7/1992 | Brockbank | |
| 5,364,756 A | 11/1994 | Livesey et al. | |
| 5,418,130 A * | 5/1995 | Platz et al. | 435/2 |
| 5,587,490 A * | 12/1996 | Goodrich et al. | 549/282 |
| 5,629,145 A | 5/1997 | Meryman | |
| 5,709,992 A | 1/1998 | Rubinstein | |
| 5,827,741 A | 10/1998 | Beattie et al. | |
| 5,843,780 A | 12/1998 | Thomson | |
| 5,863,715 A | 1/1999 | Rajotte et al. | |
| 5,869,092 A | 2/1999 | Hays et al. | |
| 5,873,254 A | 2/1999 | Arav | |
| 5,897,987 A | 4/1999 | Oliver et al. | |
| 5,955,257 A | 9/1999 | Burger et al. | |
| 6,007,978 A | 12/1999 | Goodrich, Jr. et al. | |
| 6,073,540 A | 6/2000 | Garrett | |
| 6,146,890 A | 11/2000 | Danon | |
| 6,319,914 B1 | 11/2001 | Simpkins et al. | |
| 6,337,205 B1 | 1/2002 | Wisniewski | |
| 6,453,683 B1 | 9/2002 | Wisniewski et al. | |
| 6,482,585 B2 | 11/2002 | Dottori | |
| 6,488,033 B1 | 12/2002 | Cerundolo | |
| 6,723,497 B2 | 4/2004 | Wolkers et al. | |
| 6,740,484 B1 | 5/2004 | Khirabadi et al. | |
| 6,887,704 B2 | 5/2005 | Peled et al. | |
| 2002/0119946 A1 | 8/2002 | Gen | |
| 2002/0177116 A1 | 11/2002 | Wiggins et al. | |
| 2003/0059338 A1 | 3/2003 | Mann et al. | |
| 2003/0068416 A1 * | 4/2003 | Burgess et al. | 426/384 |
| 2004/0006999 A1 | 1/2004 | Brown et al. | |
| 2004/0067157 A1 | 4/2004 | MacPhee et al. | |
| 2004/0129003 A1 | 7/2004 | Voute et al. | |

(Continued)

FOREIGN PATENT DOCUMENTS

DE  100 56 181 C1  3/2002

(Continued)

OTHER PUBLICATIONS

Towns, "Moisture content in proteins: its effects and measurement", J. of Chromatography A 705 : 115-127 (1995).*

(Continued)

*Primary Examiner*—Sandra Saucier
(74) *Attorney, Agent, or Firm*—The Nath Law Group; Susanne M. Hopkins; Ari G. Zytcer

(57) ABSTRACT

The invention provides a method for the sterilization of a biological preparation comprising desired viable biological entities. The method comprises irradiating a dried (e.g. freeze-dried) biological preparation with ionizing or UV radiation at an intensity and for a duration sufficient to reduce the amount or activity of living-matter contaminants in the biological preparation, the intensity and duration selected such that at least part of the desired biological entities in the sample remains viable. The method of the invention is particularly suitable for the reduction of the amount or activity of contaminants such as bacteria or viruses from biological preparations comprising red blood cells or platelets.

8 Claims, No Drawings

U.S. PATENT DOCUMENTS

| | | | |
|---|---|---|---|
| 2004/0191754 | A1 | 9/2004 | Meir et al. |
| 2004/0197310 | A1 | 10/2004 | Sanberg et al. |
| 2005/0008623 | A1 | 1/2005 | Bechetoille et al. |
| 2005/0020524 | A1 | 1/2005 | Boyd |
| 2005/0042754 | A1 | 2/2005 | Miyazaki et al. |
| 2005/0059152 | A1 | 3/2005 | Tanavde et al. |
| 2005/0095228 | A1 | 5/2005 | Fraser et al. |
| 2005/0118712 | A1 | 6/2005 | Tsai et al. |
| 2005/0142118 | A1 | 6/2005 | Wernet |
| 2006/0035383 | A1* | 2/2006 | Ho et al. .................. 436/69 |
| 2006/0057555 | A1 | 3/2006 | Damari et al. |
| 2007/0077237 | A1 | 4/2007 | Damari et al. |
| 2007/0077535 | A1 | 4/2007 | Wichmann et al. |
| 2008/0120984 | A1 | 5/2008 | Shaham et al. |

FOREIGN PATENT DOCUMENTS

| | | |
|---|---|---|
| EP | 0 664 080 A1 | 7/1995 |
| EP | 0 668 013 A2 | 8/1995 |
| EP | 1 057 405 A1 | 12/2000 |
| EP | 1 131 998 A1 | 9/2001 |
| EP | 1 471 140 A1 | 10/2004 |
| EP | 1 535 514 A1 | 6/2005 |
| EP | 1 627 565 A1 | 2/2006 |
| GB | 1 279 356 | 6/1972 |
| JP | 2000-189155 A | 7/2000 |
| WO | 91/06213 A1 | 5/1991 |
| WO | WO 91/16060 * | 10/1991 |
| WO | 93/00806 A1 | 1/1993 |
| WO | 97/35472 A1 | 10/1997 |
| WO | 97/39104 A1 | 10/1997 |
| WO | 98/10231 A1 | 3/1998 |
| WO | 98/46072 A1 | 10/1998 |
| WO | 99/60849 A1 | 12/1999 |
| WO | 00/29551 A2 | 5/2000 |
| WO | 01/23532 A1 | 4/2001 |
| WO | 01/45503 A2 | 6/2001 |
| WO | 01/50852 A2 | 7/2001 |
| WO | 01/87062 A2 | 11/2001 |
| WO | 02/01952 A1 | 1/2002 |
| WO | 02/32225 A2 | 4/2002 |
| WO | 02/076206 A2 | 10/2002 |
| WO | 03/020874 A2 | 3/2003 |
| WO | 03/056919 A2 | 7/2003 |
| WO | 03/099040 A1 | 12/2003 |
| WO | 2004/009138 A2 | 1/2004 |
| WO | 2004/055456 A1 | 7/2004 |
| WO | 2004/098285 A2 | 11/2004 |
| WO | 2005/032251 A1 | 4/2005 |
| WO | 2005/056755 A2 | 6/2005 |
| WO | 2005/072523 A2 | 8/2005 |
| WO | 2005/072790 A1 | 8/2005 |
| WO | 2006/016372 A1 | 2/2006 |
| WO | 2008/032314 A2 | 3/2008 |

OTHER PUBLICATIONS

Zoberi et al., "Radiosensitizing and anti-proliferative effects of resveratrol in two human cervical tumor cell lines", Cancer Letters 175 : 165-173 (2002).*

Goodrich et al. "Preservation of metabolic activity in lyophilized human erythrocytes", Proc. Natl. Acad. Sci. 89 : 967-971 (1992).*

Ahlenstiel, et al., "Bioflavonoids attenuate renal proximal tubular cell injury during cold preservation in Euro-Collins and University of Wisconsin solutions", Kidney International, vol. 63, pp. 554-563, (2003). XP-002337114.

Chen, et al., "Beneficial Effect of Intracellular Trehalose on the Membrane Integrity of Dried Mammalian Cells", Cryobiology, vol. 43, pp. 168-181, (2001).

Chow, et al., "Phase I Pharmacokinetic Study of Tea Polyphenols following Single-dose Administration of Epigallocatechin Gallate and Polyphenon E", Cancer Epidemiology, Biomarkers & Prevention, vol. 10, pp. 53-58, (2001).

Crowe, et al., "Stabilization of membranes in human platelets freeze-dried with trehalose", Chemistry and Physics of Lipids, vol. 122, pp. 41-52, (2003).

Csönge, et al., "Banking of osteochondral allografts, Part II. Preservation of Chondrocyte Viability During Long-Term Storage", Cell and Tissue Banking, vol. 3, pp. 161-168, (2002). XP-002313332.

De Korte, et al., "Quality Determinants of Erythrocyte Destined for Transfusion", Cellular and Molecular Biology, vol. 50, No. 2, pp. 187-195, (2004).

Fujiki, et al., "Mechanistic Findings of Green Tea as Cancer Preventive for Humans", P.S.E.B.M., vol. 220, pp. 225-228, (1999).

Galati, et al., "Prooxidant activity and cellular effects of the phenoxyl radicals of dietary flavonoids and other polyphenolics", Toxicology, vol. 177, pp. 91-104, (2002).

Gao, et al., "Development of a Directional Solidification Device for Cell Cryopreservation", Cell Preservation Technology, vol. 1, No. 4, pp. 231-238, (2003).

Goodrich, et al., "Preservation of metabolic activity in lyophilized human erythrocytes", Proc. Natl. Acad. Sci. USA, vol. 89, pp. 967-971, (1992).

Grinberg, et al., "Protective Effects of Tea Polyphenols against Oxidative Damage to Red Blood Cells", Biochemical Pharmacology, vol. 54, pp. 973-978, (1997).

Han, et al., "Protection of osteoblastic cells from freeze/thaw cycle-induced oxidative stress by green tea polyphenol", Biotechnology Letters, vol. 27, pp. 655-660, (2005).

Higgs, et al., "Cartilage Regeneration and Repair, Where Are We?" Proceedings of the International Cartilage Repair Society's Second Symposium, (1998).

Isbrucker, et al., "Safety studies on epigallocatechin gallate (EGCG) preparations. Part 3: Teratogenicity and reproductive toxicity studies in rats", Food Chemical Toxicology, vol. 44, pp. 651-661, (2006).

Jomha, et al., "Cryopreservation of intact human articular cartilage", Journal of Orthopaedic Research, vol. 20, pp. 1253-1255, (2002).

Kumazawa, et al., "Direct Evidence of Interaction of a Green Tea Polyphenol, Epigallocatechin Gallate, with Lipid Bilayers by Solid-state Nuclear Magnetic Resonance", Biosci. Biotechnol. Biochem., vol. 68, No. 8, pp. 1743-1747, (2004).

Kusakabe, et al., "Maintenance of genetic integrity in frozen and freeze-dried mouse spermatozoa", Proc Natl Acad Sci U S A, vol. 98, No. 24, pp. 13501-13506, (2001).

Kushibe, et al., "Tracheal Allotransplantation Maintaining Cartilage Viability with Long-Term Cryopreserved Allografts", Ann Thorac Surg, vol. 71, pp. 1666-1669, (2001).

Laprade, et al., "Refrigerated Osteoarticular Allografts to Treat Articular Cartilage Defects of the Femoral Condyles. A Prospective Outcomes Study", J Bone Joint Surg Am, vol. 91, pp. 805-811, (2009).

Lelkens, et al., "Stability after thawing of RBCs frozen with the high- and low-glycerol method", Transfusion, vol. 43, pp. 157-164, (2003).

López, et al., "Determination of Viability of Human Cartilage Allografts by a Rapid and Quantitative Method Not Requiring Cartilage Digestion", Cell Transplantation, vol. 17, pp. 859-864, (2008).

McGoveran, et al., "Long-Term Chondrocyte Viability in a Fresh Osteochondral Allograft", The Journal of Knee Surgery, vol. 15, No. 2, pp. 97-100, (2002).

Muldrew, et al., "Localization of Freezing Injury in Articular Cartilage", Cryobiology, vol. 31, pp. 31-38, (1994).

Muldrew, "Cryopreservation of Articular Cartilage", Abstracts, 33rd Annual Meeting of the Society for Cryobiology, pp. 616-617, No. 6, Indianapolis, Indiana, Aug. 21, 1996.

Muldrew, et al., "Cryobiology of Articular Cartilage: Ice Morphology and Recovery of Chondrocytes", Cryobiology, vol. 40, pp. 102-109, (2000).

Muldrew, et al., "Transplantation of Articular Cartilage Following a Step-Cooling Cryopreservation Protocol", Cryobiology, vol. 43, pp. 260-267, (2001).

Muldrew, et al., "Chondrocyte Sensitivity to Lethal Injury Correlates with Proximity to the Cartilage Surface", Abstracts, 32nd Annual Meeting of the Orthopaedic Research Society, pp. 589, No. 136, New Orleans, Louisiana, Feb. 1986.

Pegg, et al., "Fractures in Cryopreserved Elastic Arteries", Cryobiology, vol. 34, pp. 183-192, (1997).

Rzepakovsky, "The Effect of Long Term Storage at -80° C on the Cell Viabillity in Cartilage Tissue", Study Report, No. LAB-0161, 3 pages, (2005).

Rzepakovsky, "The Effect of Long Term Storage in Liquid Nitrogen on the Cell Viabillity in Cartilage Tissue", Study Report, No. LAB-0161, 3 pages, (2006).

Satpathy, et al., "Loading red blood cells with trehalose: a step towards biostabilization", Cryobiology, vol. 49, pp. 123-136, (2004).

Schachar, et al., "Transplantation of Cryopreserved Osteochondral Dowel Allografts for Repair of Focal Articular Defects in an Ovine Model", The Journal of Bone and Joint Surgery, Inc., vol. 17, pp. 909-920, (1999).

Dimethyl sulfoxide, SIGMA Product Information, 2 pages, Dec. 2003.

Suganuma, et al., "Green tea and cancer chemoprevention", Mutation Research, vol. 428, pp. 339-344, (1999).

Teng, et al., "Enhancing Osteochondral Allograft Viability", Clin Orthop Relat Res, vol. 466, pp. 1804-1809, (2008).

Van Steensel, et al., "Optimization of cryopreservative procedures for human articular cartilage chondrocytes", Arch Orthop Trauma Surg, vol. 113, pp. 318-321, (1994).

Williams, et al., "Prolonged Storage Effects on the Articular Cartilage of Fresh Human Osteochondral Allografts", J Bone Joint Surg Am, vol. 85, pp. 2111-2120, (2003).

Williams, et al., "Analysis of Cartilage Tissue on a Cellular Level in Fresh Osteochondral Allograft Retrievals", Am J Sports Med, vol. 35, No. 12, pp. 2022-2032, (2007).

Williams, et al., "Controversies in Knee Surgery", Controversies in Orthopaedic Surgery, pp. 462-463, Oxford University Press, 2004.

XP-002337043: DERWENT, "Preservation solution for cells and tissues contains polyphenol as effective component", 1 page, (2002).

XP-002337044: DERWENT, "Composition for preservative of animal cell, organs such as skin, blood vessel, cornea, kidney, heart, liver, lungs, placenta or pancreas, contains preset amount of epigallocatechin gallate as active ingredient", 1 page, (2003).

Zoberi, et al., "Radiosensitizing and anti-proliferative effects of resveratrol in two human cervical tumor cell lines", Cancer Letters, vol. 175, pp. 165-173, (2002).

* cited by examiner

METHOD FOR STERILIZING LYOPHILIZED EUKARYOTIC ANUCLEAR CELLS WITH GAMMA IRRADIATION

CROSS-REFERENCE

This is a National Phase Application filed under 35 U.S.C. 371 of International Application No. PCT/IL2005/000600, filed Jun. 7, 2005, claiming the benefit under 35 USC 119(e) of U.S. Provisional Application No. 60/577,210, filed Jun. 7, 2004, the entire contents of each of which is hereby incorporated herein by reference in its entirety.

FIELD OF THE INVENTION

The invention relates to the sterilization of biological preparations. More specifically the present invention relates to a method for the sterilization of biological preparations and to sterilized biological preparations.

LIST OF REFERENCES

The following references are considered to be pertinent for the purpose of understanding the background of the present invention:
1. US 2004/067157 Methods for Sterilizing Biological Materials;
2. WO 2004/009138 Methods for Sterilizing Milk;
3. PCT IL2005/000125 Biological Material and Methods and Solutions for Preservation Thereof
4. U.S. Pat. No. 5,709,992 Method for disinfecting red blood cells;
5. U.S. Pat. No. 6,482,585 Storage and maintenance of blood products including red blood cells and platelets;
6. Hustom, et al. *Lack of efficacy for conventional gamma irradiation of platelet concentrates to abrogate bacterial growth*. Am J Clin Pathol. 1998; 109(6):743-7
7. Smith, et al. *Gamma irradiation of HIV*-1. J orthop Res. 2001; 19(5): 815-9.

BACKGROUND OF THE INVENTION

When storing cells, tissue or other biological material, there is always the danger of contamination from bacteria, viruses, yeasts, molds, fungi etc., and sometimes the contaminants are present in the biological material when it is first collected. Contaminants are such agents that may damage the biological material during preservation and/or harm the recipient when the product is used (e.g. transfused, injected or eaten). Among known contaminants are white blood cells (WBC) that are normally present in red blood cell (RBC) samples. The presence of WBC in a transfusion liquid is a problem due to graft vs. host disease, in which the transfused WBC (mainly the lymphocytes) attack the recipient's body.

Many methods for sterilization are known in the art including heating and filtration. However, these processes may damage biological material (e.g. when it is sensitive to heat) or prove to be inefficient (e.g. when the biological material is filtered with some contaminants). Other ways for sterilization involve ionizing radiation, mainly gamma rays. For example, gamma radiation is used for inactivation of WBC, mainly the lymphocytes which are the main cause for graft versus host disease (GVHD), in fresh blood units. This is normally done by irradiating a liquid sample of blood or blood components including RBC, platelets, granulocyte components and non frozen plasma in a plastic bag with 2.5 mega Rad of gamma radiation to the central portion of the bag, resulting with no less than 1.5 mega Rad which are delivered to every part of the blood bag (AABB Technical Manual, $14^{th}$ edition). Attempts were made to reduce the bacteria content in platelet concentrates (Hustom et al. 1998) but it was concluded that exposure to gamma radiation at levels up to 7.5 mega Rad was ineffective at sterilizing the sample. Likewise it was found that gamma radiation (1.5-2.5 mega Rad) does not constitute a virucidal dose for HIV type 1 in frozen bone and tendon allografts (Smith et al. 2001).

Furthermore, gamma radiation can be damaging to radiation-sensitive products. In particular it has been shown that gamma radiation is injurious to red blood cells, platelets and granulocytes (US 2004/067157).

Ultraviolet (UV) radiation on the other hand is considered less damaging than gamma radiation. However, as UV radiation is absorbed by water, it is practically ineffective for removal of contaminants that are in a water-containing sample (liquid or ice). Accordingly it was suggested in WO 2004/0091938 that reduction of the residual solvent content of biological material would reduce the absorption of UV in the water and thus enable sterilization of a biological sample using V. However, sterilization of biological material in WO 2004/0091938 was restricted to wet biological material or to non-cellular portions of a blood preparation (i.e. not including RBC or platelets), apparently since "sensitive biologicals, such as blood, would lose viability and activity if subjected to freezing for irradiation purposes and then thawing prior to administration to a patient" (id.).

GLOSSARY

The term "biological preparation" denotes a preparation or sample (natural, processed or man made) comprising desired biological entities. "Desired biological entities" are viable nucleus free biological entities, including eukaryotic nucleus free cells (e.g. RBC), parts of cells (e.g. platelets), or artificial or semi-artificial material such as liposomes. Examples of such biological preparations include blood or fractions thereof that contain RBC or platelets, an RBC-enriched fraction of blood, packed RBC or platelet-enriched fraction of blood, samples of liposomes, etc.

A "Viable" biological preparation is such that at least a portion of the desired biological entities therein appear to be structurally intact, or preferably that they at least partially retain a desired biological activity or if in a dry state may resume that activity upon rehydration. Preferably at least 10% of the desired biological entities are viable, desirably at least 30% or even at least 50%. In the case of RBC for example a preferred percentage of viable cells may in some cases be at least 75%.

In this invention, "liposomes" mean hollow lipid vesicles. They may be used to entrap the substance to be delivered within the liposomes, or the drug molecule of interest can be incorporated into the lipid vesicle as an intrinsic membrane component, rather than entrapped into the hollow aqueous interior, or electrostatically attached to the aggregate surface.

The term "living-matter contaminants" is taken to mean biological entities that contain genetic material and are therefore radiation sensitive. The living-matter contaminants may be present in a biological preparation, either at the time of harvesting or may contaminate the biological preparation at a later time (e.g. during its manipulation or storage), and may damage the biological preparation or a portion thereof, its recipient or otherwise interfere with the use of the biological preparation. Such living-matter contaminants may be any type of biological entity including, nucleic acid sequences, prokaryotes including viruses, mycoplasma or bacteria and, fungi, yeasts, molds, single cell or larger parasitic microorganisms, or other undesired cellular entities, such as WBC, etc.

The "Activity" of contaminants means any activity that may damage the biological preparation, its recipient or otherwise interfere with the use of the biological preparation (including due to legal constraints). The contaminants are of such radiation sensitivity that upon irradiation they are reduced in number or activity, for example by becoming less likely to multiply (e.g. bacteria, WBC, yeast) or less likely to infect target cells (e.g. viruses) or transfect cells (nucleic acid sequences) or less likely to display a significant immune effect (e.g. WBC). The amount or activity of the contaminants may be assayed, directly or indirectly, using any method of the art.

The term "ionizing radiation" means any form of radiation that has enough energy to remove electrons from substances it passes through, forming ions. This includes alpha and beta particles, gamma radiation and x-rays. The term "UV radiation" means radiation having a wavelength between 100-400 nm. It includes three ranges: UV-A (315-400 nm), UV-B (280-315 nm) and UV-C (100-280 nm).

The terms "drying" "dried" or "dry" mean having (or causing to have) a reduced water content as compared to the water content before drying. A dried preparation may have 10% less water than the original preparation from which it was derived, preferably less than 60% or even 75%, and desirably 90% less water than the original preparation. Drying may be done using any method known in the art, including air drying, heat drying, freeze drying, spray drying or nebulizing, as long as the biological preparation maintains viability of the desired biological entities. Examples of methods include air drying of liposomes (Hincha et al. 2003; *Biochemica et Biophysica ACTA.* 1612(2):172-177), embryonic kidney cell line and human foreskin fibroblasts cells (Gau et al. 2000; *Nature Biotechnology.* 18:168-171) etc. It is noted that bacteria may survive the air-drying process (Desmond et al. *J Appl Microbiol.* 2002; 93(6):1003-11) and so can other contaminants.

The terms "lyophilization" or "freeze-drying" denote a process wherein material is frozen and dried. Thus, in the present invention wherever a biological preparation is said to be freeze dried or lyophilized, this may mean that at least two steps were executed, one of which for freezing the sample and the other for drying. Each of these steps may be done using any known method, and preferably such known methods that cause minimal damage to the desired biological entities. Preferred methods of freeze-drying are disclosed in PCT IL2005/000125, the content of which is incorporated herein in full by way of reference.

SUMMARY OF THE INVENTION

The present invention is based on the inventors' surprising finding that biological preparations comprising desired nucleus free biological entities, such as RBC or platelets, may be irradiated using ionizing or UV radiation, when in a dried (e.g., freeze-dried) state such that undesired living-matter contaminants will be destroyed with relatively little damage to said biological entities. "Little damage" should be taken to mean that at least 10% of the desired biological entities are viable, desirably at least 30% or even at least 50% of said biological entities is viable after irradiation. The invention is particularly suitable for biological preparations that are freeze dried and rehydrated as described in PCT application PCT IL2005/000125, the contents of which is incorporated herewith by reference in full, albeit not limited thereto. The invention permits, according to an embodiment thereof, the irradiation and sterilization of biological preparations comprising desired nucleus free biological entities using ionizing or UV irradiation.

Thus, the present invention provides according to one aspect a method for the sterilization of a biological preparation comprising desired viable biological entities, the method comprising irradiating a dried biological preparation with ionizing or UV radiation at an intensity and for a duration sufficient to reduce the amount or activity of living-matter contaminants in the biological preparation, the intensity and duration selected such that at least part of the desired biological entities in the sample remains viable.

The present invention is particularly suitable for biological preparations comprising desired biological entities derived from blood, including RBC and platelets.

DETAILED DESCRIPTION OF THE INVENTION

As detailed above, the present invention provides a method for the sterilization of biological preparations comprising desired viable biological entities, allowing reduction of the amount or activity of living-matter contaminants in the biological preparation. Potentially, the amount of active contaminants in the biological preparation is reduced to none. In cases when a single biological preparation comprises one or more contaminants before irradiation, it is intended that the method of the present invention would allow the reduction of the amount or activity of at least one of said contaminants. Furthermore, in some cases, before irradiation the biological preparation might be free of active contaminants, in which case the present invention would ensure the lack of contaminants and thus diminish, or even negate, the need to check for active contaminants.

According to some embodiments, the method also includes a step of drying a biological preparation comprising desired viable biological entities. It is hence noted that the step of irradiating the biological preparation may be performed at any time after the biological preparation will become dry or partially dried. In fact, the irradiating may be done simultaneously (or partially simultaneously) with or even in between two steps of drying the biological preparation.

Any type of ionizing or UV radiation may be suitable for the present invention, however a person skilled in the art would appreciate that the type, intensity and duration of irradiation would best be chosen so as to retain as much as possible the viability of the biological preparation while reducing as much as possible the amount or activity of contaminants.

In order to understand the invention and to see how it may be carried out in practice, preferred embodiments will now be described, by way of non-limiting example only.

EXPERIMENTS

Materials and Methods

Unless otherwise noted, all materials were purchased from Sigma Inc. (St. Louis. Mo., USA).

Example 1

The Effect of UV Exposure on the Survival of Lyophilized RBC

The effects of irradiation and freeze drying on red blood cells (RBC) were evaluated in this experiment. The freezing solution used was composed of 30% (w/v) dextran in PBS ($Ca^{2+}$ and $Mg^{2+}$ free). Packed RBC obtained from the Israeli Blood Services were mixed at a ratio of 1:1 (v/v) with the freezing solution. 2.5 ml of RBC solution was put in a 16 mm diameter of glass test tubes (Manara, Israel) which were then frozen. Freezing was done using the MTG freezing device (IMT, Israel) at a cooling rate of 1000° C./min; (thermal gradient) G=5.5° C./mm, V=3 mm/sec. The samples were also rotated at 56 RPM (rounds per minute).

After freezing, samples were put in a lyophilizer (Labconco, USA) for 3 days (condenser −80° C.). After 3 days of lyophilization, when the samples contained 10% or less of their original water content, one sample was placed in a Petri dish and exposed to UV radiation for 1 hour and the other was protected from light using aluminum foil. After 1 hour irradiation the samples were rehydrated with ultra pure water at 37° C. to their original volume. RBC were counted and hematocrit assayed using the Pentra 60 (ABX, France).

TABLE I

Effect of UV exposure on lyophilized RBC

|  | Lyophilized RBC | |
| --- | --- | --- |
|  | exposed to UV | not exposed to UV |
| Amount of cells | 52.04% | 57.6% |
| hematocrit | 29.2% | 35.5% |

The results are shown as a percentage of the fresh sample, before freezing.

As seen in Table I the sample that was exposed to UV exhibited a slightly lower survival rate than that of the sample that was not exposed to radiation. Since the inventors discovered that addition of polyphenols to the freezing solution improves the cells' survival in freeze-drying—thawing treatments, in the following experiments one such polyphenol was added to the biological samples. The term "polyphenols" denotes one or more natural and/or synthetic polyphenols that may be naturally found in green tea, including epigallocatechin gallate (EGCG), epicatechin gallate (ECG) epigallocatechin (EGC) epicatechin (EC).

Example 2

The Effect of UV Radiation on Lyophilized RBC Survival

In this experiment packed RBC were frozen with a freezing solution containing: 30% (w/v) dextran 40,000 Dalton and 0.47 mg/ml EGCG (Cayman Chemical, USA). The freezing solution and the packed RBC were mixed in a ratio of 1:1 (v/v). 2.5 ml of the cell suspension were put in 16 mm diameter glass test tubes (Manara, Israel). A total of 4 test tubes were frozen. The samples were frozen at a cooling rate of 1000° C./min; (thermal gradient) G=5.5° C./mm, V=3 mm/sec using the MTG Device (IMT, Israel). The samples were also rotated at 56 RPM.

After freezing, samples were placed in liquid nitrogen. After the passage of varying time periods (between ½ hour to a few weeks) samples were placed in a lyophilizer (Labconco, USA) with a condenser temp of −80° C.) for 72 hours, and the samples were dried such that they had the appearance of a powder and had less than 10% of their original water content. Then samples were transferred to a 60 mm Petri dish, 2 samples were exposed to UV for 1 hour and during that 1 hour the other 2 samples were covered with aluminum foil to prevent exposure to light. All samples were then rehydrated with ultra pure water at 37° C. to their original volume and compared using the PENTRA 60 counter (ABX, France). Results are presented as compared to the parameters of fresh RBC in a freezing solution including EGCG.

TABLE II

Effect of UV radiation on lyophilized RBC survival

|  | Lyophilized RBC | |
| --- | --- | --- |
|  | no UV treatment | UV treatment |
| Cells number | 58.11% | 54.05% |
| Hematocrit | 43.02% | 45.95% |

Results are shown as percentage of the fresh values of the same samples

As can be seen from Table II, although more than 50% of the RBC appeared viable, freeze-dried cells were less viable and had a lower hematocrit than fresh cells. Nevertheless, these parameters were only slightly affected by UV radiation.

Example 3

The Effect of Partial Drying on RBC Survival

Fresh whole rat's blood (extracted from Sprague-Dawley rats) was washed once. Plasma was removed and the packed RBCs were suspended in a 1:3 ratio (v/v) with a freezing solution composed of 0.945 mg/ml EGCG and 20% (w/v) Dextran 40 kD in 0.9% (w/v) NaCl solution, and the final hematocrit was 25%. Three samples (2.5 ml each) were frozen each in a 16 mm diameter glass test tube (Manara, Israel) using the MTG device (IMT, Israel), with the following parameters: velocity=3 min/sec; temperature gradient was 5.5° C./mm, the test tubes were rotated at 60 rpm. After freezing, samples were stored in LN until lyophilization. Lyophilization was done in a special lyophilization device (IMT, Israel) subject of co-pending PCT application No. IL2005/000124, which has a condenser temperature of −190° C. and samples were kept at a temperature of −20° C. Samples remained in the device for 48 hours. After 48 hours samples were taken out and thawed in a 37° C. water bath. Since, the samples were partly dried 1.5 ml 37° C. PBS ($Ca^{2+}$ and $Mg^{2+}$ Free) was added to rehydrate the cells. PBS was added instead of water since adding water is expected to cause more damage to the cells than excess PBS.

The samples were then evaluated using the Pentra 60 cell counter (ABX, France) for a complete blood count evaluation, and supernatant free hemoglobin levels were measured using the cyanmethemoglobin method using Drabkin's reagent. The absorbance was read at a wavelength of 540 nm using a luminometer (Turner Biosystems, USA). The percentage of the supernatant free hemoglobin (Hb) was calculated using the following Formula I:

$$\% \text{ Free hemoglobin} = 100 \times \frac{\text{(Absorbance of the supernatant)}}{\text{(Absorbance of supernatant} + \text{Absorbance of the pellet)}} \quad \text{Formula I}$$

TABLE III

Partially dried RBC samples

| Rat RBCs | % Water loss | Free Hb (%) | MCV (%)* | Cell number (%)* |
|---|---|---|---|---|
| Fresh (3:1 ratio) | — | 5.89 | — | — |
| Lyophilized | 60% | 22.26 ± 0.16 | 76.60 | 78.63 |

*Results given as percentages of thawed values as compared to fresh values.

Lyophilization for 48 hours resulted in about 60% of water loss. This water loss was evaluated by the amount of PBS that was needed to be added to the solution in order to regain the original sample's volume. In the freeze dried sample there was some cell damage as seen in the free hemoglobin percentage (22.26% Free Hb). However, microscopic observations revealed more than 50% of the cells with normal morphology. In addition, this free hemoglobin rate might be a result of the thawing process, since upon thawing and before addition of PBS the thawed cells were exposed to a very hypertonic environment, which remained hypertonic but to a lesser extent after PBS was added.

Example 4

The Effect of Freezing and Freeze-Drying on E. coli

E. coli were placed in LB medium: 10 gr Bacto-tryptone (Difco, USA), 5 gr yeast extract (Difco, USA), 10 gr NaCl, in 1 liter distilled water. The total volume of 10 ml was divided to two batches of 5 ml each. To the first batch of E. coli in LB medium we added 5 ml of freezing solution composed of 30% (w/v) dextran and 0.47 mg/ml EGCG (Cayman Chemical, USA) in PBS ($Ca^{+2}$ and $Mg^{+2}$ free). The other batch was left un-touched. Cell-suspension samples of 2.5 ml each (two from each batch) were put in 16 mm diameter glass test tubes (Manara, Israel), such that a total of 4 test tubes were prepared. The test tubes were frozen using the MTG Device (IMT, Israel) at 1000° C./min (from 5 to −50° C. at a velocity of 3 mm/sec and with 56 RPM. After freezing was completed the test tubes were placed in liquid nitrogen. Afterwards, the 4 test tubes were placed in a lyophilizer (Labcono, USA) for 72 hours. After lyophilization was completed the "powdered" cells from each test tube were scraped into a Petri dish. Two Petri dishes (one representing each batch) were exposed to UV radiation for 1 hour (the Petri dishes were placed opened under a UV lamp) and the other two Petri dishes were left unexposed to radiation (covered with aluminum foil for protection from light). After 1 hour 2 ml of double distilled water at 37° C. were added to each dish. From each dish 3 Petri dishes with agar were plated. The following Agar plates protocol was used: 10 gr Bacto-tryptone, 5 gr yeast extract, 10 gr $Na^+$ $Cl^-$, 10 gr agar (BD, USA). Water was added to a volume of 1 liter, autoclaved, cooled to 65° C. and poured into Petri dishes. A total of 12 Petri dishes were incubated at 37° C. for 24 hours. The next day colonies were counted. Table IV depicts the number of colonies grown on the agar Petri dishes.

TABLE IV

Number of E. coli colonies after being frozen with different freezing solutions and lyophilized

| E. coli frozen in LB | | E. coli frozen with dextran and EGCG | |
|---|---|---|---|
| — | UV | — | UV |
| 36 | 0 | 152 | 0 |
| 24 | 0 | 220 | 0 |
| 16 | 0 | >200 | 0 |

As seen in Table IV, E. coli colonies were observed only in the plates of the un-irradiated bacteria. No colonies were observed in the agar plated with lyophilized cells that were irradiated. In addition, the addition of Dextran and EGCG results in higher survival rates of the bacteria after lyophilization.

Example 5

The Effect of Freezing and Freeze-Drying on E. coli in an RBC Preparation 10 ml of E. coli in LB medium was centrifuged at 800 g for 10 minutes. To the resultant pellet 10 ml of freezing solution composed of 30% (w/v) dextran 40,000 Dalton and 0.47 mg/ml EGCG (Cayman Chemical, USA) in PBS ($Ca^{+2}$ and $Mg^{+2}$ free) were added. This solution was then mixed in a volumetric ratio of 1:1 with packed RBC. 2 ml of RBC & E. coli were put in a Petri dish; a total of 4 like dishes were prepared. 2 Petri dishes were exposed to UV for 1 hour and the other 2 were not. After 1 hour cells from each group were plated on three agar plates that were placed in a 37° C. oven for 24 hours.

From the remaining RBC-coli mixture four test tubes were prepared, each containing 2.5 ml. The test tubes were frozen using the MTG device (IMT, Israel) at 1000° C./min (from 5 to −50° C. at a velocity of 3 mm/sec and with 56 RPM and then placed in a lyophilizer for 72 h. After lyophilization one test tube from each group was exposed to UV radiation for 1 hour. After 1 hour 2 ml of $ddH_2O$ was added and from each group 3 agar plates were seeded and placed for 24 hour in 37° C. oven for 24 hours. The results are depicted in Table IV.

TABLE V

The effect of UV radiation on the survival of E. coli in lyophilized or fresh samples comprising RBC

| Fresh RBC and E. coli | | Lyophilized RBC and E. coli | |
|---|---|---|---|
| — | UV | — | UV |
| >200 | >200 | >200 | 0 |
| >200 | >200 | >200 | 0 |
| >200 | >200 | >200 | 0 |

As seen in Table V irradiation in the liquid state had no measured effect on E. coli, as in all plates more then 200 colonies were observed. However, when irradiated in a dry (lyophilized) state no colonies were observed after 24 hours in incubation.

Example 6

The Effect of UV Radiation on the Survival of *E. coli* in Fresh Platelets Concentrates A unit of fresh platelets was received from the Israeli blood bank. Platelets were added to an *E. coli* pellet (*E. coli* in LB medium that was centrifuged for 10 minutes at 2000 g). The platelets & *E. coli* solution was mixed at a ratio of 1:1 (v/v) with a freezing solution composed of 30% (w/v) Dextran (40,000 Dalton; Amersham Biosciences, USA) and 1.87 mg/ml EGCG (Cayman, USA) in PBS (calcium and magnesium free). Two samples, 2.5 ml each, of platelet suspension were put in a 60 mm Petri dish. One dish was exposed to UV radiation for 1 hour, and the other was left untouched, covered in aluminum foil. After one hour, samples from each Petri dish were seeded in agarose and put in an incubator at 37° C. for 24 hours. After 24 hours colonies were counted.

TABLE VI

The effect of UV radiation on the number of *E. coli* colonies

| Exposed to UV | Not exposed to radiation |
| --- | --- |
| 269 | 201 |

We can see that UV irradiation of *E. coli* in a fresh platelet concentrate did not have an effect on the *E. coli* survival, resulting in 269 colonies in the sample that was exposed to radiation and in 201 in the sample that were not exposed to UV radiation.

Example 7

The Effect of UV Radiation on the Number of *E. coli* Colonies Grown after being Lyophilized Platelets-*E. coli* solutions were prepared as described in Example 6. The platelets-*E. coli* solution was divided to two batches, and each batch was mixed at a ratio of 1:1 (v/v) with one of the following freezing solutions: (1) 30% (w/v) Dextran (40 KDa) and 1.87 mg/ml EGCG in PBS (calcium and magnesium free); or (2) 30% (w/v) Dextran (40 KDa) in PBS (calcium and magnesium free). 2.5 ml aliquots of platelet suspension were put in 16 mm diameter glass test tubes (Manara, Israel). A total of 4 test tubes were prepared, 2 tubes from each batch. The tubes were frozen in the MTG device at a thermal gradient of 5.5° C./mm and at a cooling rate of 1000° C./min (final temperature was −50° C., velocity was 3 mm/sec).

After freezing, all tubes were maintained in liquid nitrogen and later lyophilized for 3 days, such that the preparation appeared as a powder containing less than 10% of its original water content. The resultant dry powder was scraped into a 60 mm Petri dish, such that two dishes were prepared from each of the above batches. One dish from each batch was exposed to UV radiation for 1 hour. The other 2 dishes (one from each batch) were untouched, covered in aluminum foil. The contents of each Petri dish were rehydrated with 2 ml of ultra pure water at 37° C. and a sample from each dish was seeded in agarose and incubated at 37° C. for 24 hours. After 24 hours colonies were counted.

TABLE VII

The effect of UV radiation on the number of *E. coli* colonies grown after being lyophilized

| batch | UV | No UV |
| --- | --- | --- |
| Platelets - *E. coli* & Dextran 30% | 1 | 17 |
| Platelets - *E. coli* & Dextran + EGCG | 1 | 11 |

As seen in Table VII, UV radiation reduced the number of colonies by more than tenfold.

In order to assess the platelets' survival of the UV irradiation in a dry state, samples of platelets (prepared with EGCG and Dextran as described above) taken after lyophilization and rehydration were compared with those taken after UV irradiation. The platelets were counted using the Pentra 60 (ABX, France) cell counter, and it was observed that 80.38% of the platelets that survived lyophilization also survived UV treatment.

Example 8

Sterilization by Gamma Radiation of Lyophilized RBC Samples Contaminated with West Nile Virus (WNV)

Example 8A

Sterilization of RBC Using Gamma Radiation

Packed RBC that were received from the Israeli Blood Services were mixed in a volumetric ratio of 1:1 with a freezing solution composed of 20% (w/v) Dextran 40 kD and 0.945 mg/ml EGCG and 0.9% (w/v) NaCl in double distilled water. 2.5 ml samples were contaminated with WNV (received from the Israeli Veterinary Institute) to the following virus concentrations: $10^{6.8}$ WNV/ml blood (referred to Max), 105.8 WNV/ml blood (referred to as −1) and $10^{4.8}$ WNV/ml blood (referred to as −2). Uncontaminated blood was used as a control for the infection.

The 2.5 ml samples were frozen using the MTG freezing device (IMT Israel), in the same conditions as described above. After freezing was completed samples were stored in liquid nitrogen until put in a lyophilizer (condenser temperature −80° C.) (Labconco, USA) for 72 hours.

The freeze-dried blood was exposed to gamma radiation of one of three intensities (1, 2.5 and 5 mega Rad), whilst a control for the irradiation was kept without irradiation. After the irradiation all samples were rehydrated with double distilled water at 37° C. to the samples' original volume.

Survival of the viruses was assayed by injection of 0.03 ml blood samples to the brain of newborn mice. The mice were monitored for up to 14 days after infection, during which the number of mice that died after displaying WNV symptoms was recorded. The results are summarized in Table VIII

TABLE VIII

Mice mortality due to injection of Lyophilized RBCs which were contaminated with WNV

| Virus conc. | Gamma radiation amount (Mega Rad) | number of mice | mortality |
|---|---|---|---|
| max | 0 | 11 | 11 |
| −1 | 0 | 11 | 11 |
| −2 | 0 | 11 | 11 |
| none | 0 | 11 | 0 |
| max | 1 | 10 | 10 |
| −1 | 1 | 10 | 0 |
| −2 | 1 | 10 | 0 |
| none | 1 | 10 | 0 |
| max | 2.5 | 11 | 0 |
| −1 | 2.5 | 11 | 0 |
| −2 | 2.5 | 11 | 0 |
| none | 2.5 | 11 | 0 |
| max | 5 | 11 | 0 |
| −1 | 5 | 11 | 0 |
| −2 | 5 | 11 | 0 |
| none | 5 | 11 | 0 |

As can be seen in Table VIII above, irradiation of freeze dried RBC by gamma radiation has significantly reduced the activity of WNV in all the experimented levels of radiation. Even at the intensity of 1 mega Rad the radiation has reduced the WNV activity in the lower concentrations of −1 and −2 below a detectable level. This level of radiation (1 mega Rad) is well bellow what is commonly used for WBC inactivation of blood samples.

Those skilled in the art will readily appreciate that various modifications and changes can be applied to the embodiments of the invention as hereinbefore described without departing from its scope defined in and by the appended claims and their equivalents. Also, it is to be understood that the phraseology and terminology employed herein are for the purpose of description and should not be regarded as limiting.

The invention claimed is:

1. A method for sterilizing a biological preparation comprising a viable eukaryotic anuclear cell, the method comprising:
   providing a viable freeze-dried biological preparation comprising a polyphenol and the viable eukaryotic anuclear; and
   irradiating the freeze-dried biological preparation with ionizing radiation at an intensity and for a duration sufficient to reduce the amount or activity of living-matter contaminants in the biological preparation, the intensity and duration selected such that at least part of the viable biological preparation in the freeze dried biological preparation remains viable.

2. The method of claim 1, wherein the freeze-dried biological preparation comprises blood or portion thereof.

3. The method of claim 1, wherein the eukaryotic nucleus free cell is selected from the group consisting of red blood cells (RBC) or platelets.

4. The method of claim 1, wherein the living-matter contaminants are selected from the group consisting of bacteria and viruses.

5. The method of claim 1, wherein the amount or activity of living-matter contaminants is reduced.

6. The method of claim 1, wherein the ionizing radiation is gamma radiation.

7. The method of claim 6, wherein the gamma radiation is below 2.5 mega Rad.

8. The method of claim 7, wherein the gamma radiation is below 1 mega Rad.

* * * * *